(12) United States Patent
Yang et al.

(10) Patent No.: US 8,815,523 B2
(45) Date of Patent: Aug. 26, 2014

(54) METHOD FOR LIVE-CELL ACTIVITY ASSAY

(75) Inventors: Eun-Gyeong Yang, Seoul (KR); Yu-Ran Na, Seoul (KR); Hong-Kun Park, Lexington, MA (US); Jorgolli Marsela, Arlington, MA (US)

(73) Assignee: Korea Institute of Science and Technology, Seoul (KR)

( * ) Notice: Subject to any disclaimer, the term of this patent is extended or adjusted under 35 U.S.C. 154(b) by 938 days.

(21) Appl. No.: 12/900,561

(22) Filed: Oct. 8, 2010

(65) Prior Publication Data

US 2011/0165587 A1    Jul. 7, 2011

(30) Foreign Application Priority Data

Jan. 5, 2010 (KR) .................. 10-2010-0000396

(51) Int. Cl.
| | | |
|---|---|---|
| *G01N 33/53* | (2006.01) | |
| *G01N 33/543* | (2006.01) | |
| *B82Y 15/00* | (2011.01) | |
| *G01N 33/553* | (2006.01) | |
| *B82Y 5/00* | (2011.01) | |

(52) U.S. Cl.
CPC ........ *G01N 33/553* (2013.01); *G01N 33/54386* (2013.01); *B82Y 15/00* (2013.01); *B82Y 5/00* (2013.01)
USPC ........................................................ 435/7.2

(58) Field of Classification Search
None
See application file for complete search history.

(56) References Cited

U.S. PATENT DOCUMENTS

| 7,303,875 | B1 * | 12/2007 | Bock et al. .................. 435/6.11 |
|---|---|---|---|
| 8,318,297 | B2 * | 11/2012 | Tian et al. .................. 428/304.4 |
| 2002/0187504 | A1 * | 12/2002 | Reich et al. ...................... 435/6 |
| 2006/0141610 | A1 | 6/2006 | Xing et al. |
| 2008/0044911 | A1 * | 2/2008 | Bock et al. ....................... 436/63 |
| 2008/0081439 | A1 * | 4/2008 | Coffer ........................... 438/468 |
| 2008/0315175 | A1 * | 12/2008 | Pauzauskie et al. ............ 257/12 |
| 2008/0318044 | A1 * | 12/2008 | Tian et al. ..................... 428/401 |
| 2009/0124025 | A1 * | 5/2009 | Hamilton et al. ............. 436/524 |
| 2010/0282734 | A1 * | 11/2010 | Kuypers ........................ 219/482 |
| 2011/0117648 | A1 * | 5/2011 | Chiou et al. .................. 435/375 |
| 2011/0165587 | A1 * | 7/2011 | Yang et al. ..................... 435/7.1 |
| 2012/0258308 | A1 * | 10/2012 | Jeong et al. ................... 428/368 |
| 2012/0267604 | A1 * | 10/2012 | Tian et al. ......................... 257/9 |
| 2013/0216779 | A1 * | 8/2013 | Hofmeister et al. .......... 428/141 |
| 2013/0260467 | A1 * | 10/2013 | Park et al. ..................... 435/455 |

FOREIGN PATENT DOCUMENTS

KR     10-2009-0008798     1/2009

* cited by examiner

*Primary Examiner* — Ann Lam
(74) *Attorney, Agent, or Firm* — Lexyoume IP Meister, PLLC

(57) ABSTRACT

Provided are technologies capable of direct measurement of activity of a bioactive substance in cell using nanowires, more particularly, a method for measuring intracellular activity of a bioactive substance using a nanowire support to which cells are immobilized and a nanowire support to which target substances for the subject bioactive substance are immobilized, and a chip for measuring intracellular activity of a bioactive substance including nanowires to which cells are immobilized and nanowires to which a target substance for the subject bioactive substance is immobilized.

12 Claims, 8 Drawing Sheets

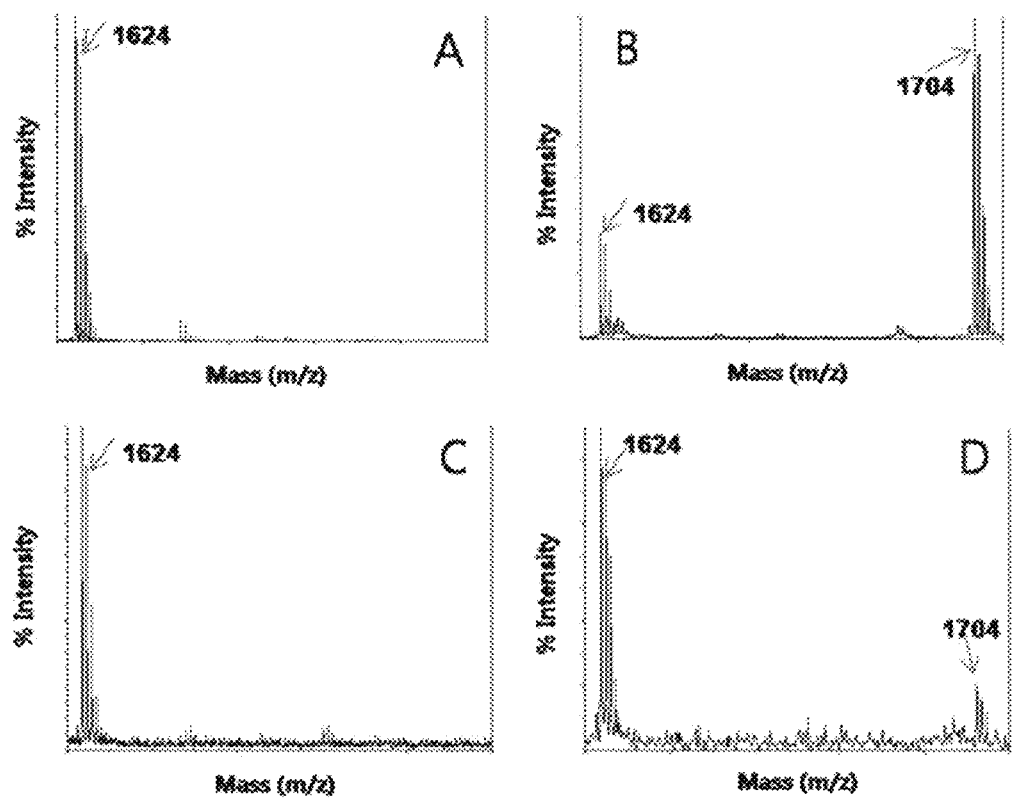

METHOD FOR LIVE-CELL ACTIVITY ASSAY

CROSS-REFERENCE TO RELATED APPLICATION

This application claims priority to and the benefit of Korean Patent Application No. 10-2010-0000396 filed in the Korean Intellectual Property Office on Jan. 5, 2010, the entire contents of which are incorporated herein by reference.

BACKGROUND OF THE INVENTION (a) Field of the Invention

This disclosure relates to technologies for direct measurement of activity of a bioactive substance in cell using nanowires. In particular, a method of measuring intracellular activity of a bioactive substance using a support having nanowires to which a cell is immobilized and another support having nanowires to which a target substance for a bioactive substance to be detected is immobilized, and a chip for measuring intracellular activity of a bioactive substance including a support having nanowires to which a cell is immobilized and another support having nanowires to which a targeting substance for a bioactive substance to be detected are immobilized, are provided.

(b) Description of the Related Art

In general, enzyme activity has been studied using purified enzymes and substrates, and the methods include spectrophotometric assays measuring absorbance changes according to changes of substrates due to enzyme activities to identify enzyme activities, fluorometric assays measuring enzyme activities using differences in fluorescence between a product produced by enzyme activity and an initial substrate, calorimetry assays measuring heat absorbed or emitted by chemical reactions to measure changes of substrates due to enzyme reactions using microcalorimeter, chemiluminescent assays measuring light emission due to chemical reactions to measure enzyme activities, chromatographic assays measuring a product generated by enzyme activity using chromatography, and radiometric assays identifying enzyme activities using radioisotopes as substrates, and the like.

Since most of the methods for measuring enzyme activity are conducted in vitro using purified enzymes and substrates, various external conditions (ionic strength, salt concentration, temperature, pH, enzyme concentration, and etc.) may be controlled to conduct assays under best conditions for enzyme activity, which differs from endogenous enzyme conditions in cells. Since the existence of large quantities of macromolecules in cells may influence functional and structural stability of protein, and enzyme reaction including rate of reaction, the result of activity analysis using purified enzyme cannot always be regarded as representing enzyme action in cells.

Moreover, since in many cases, another enzyme reversing the reaction of one enzyme exists (for example, protein kinase and phosphatase which respectively cause phosphorylation and dephosphorylation exist simultaneously in cells), enzyme activity in the cell context may not be predicted simply by in vitro cell activity analysis. Recently, for measurement of endogenous enzyme activity in cells, various methods involving instantaneous cell lysis followed by assays have been extensively employed. However, the possibility that enzyme environment and activity may be changed during the cell lysis and lysate preparation cannot be excluded, and thus a method for analysis of enzyme activity with maintaining cells alive is required.

Nanotechnology enables characterization and control of material in atomic and molecular unit, and it has recently been combined with biotechnology and developed as new technology for future. Many study results have been reported on low dimensional nanostructures, and particularly one-dimensional nanomaterials such as nanorods, nanowires, nanotubes, nanobelts and the like with excellent optical, electrical, chemical and physical properties have been applied in various fields.

So far, biomedical applications of nanotechnology have mainly been focused on elucidating characteristics of nanoparticles for bio-imaging technology, biosensor, and local drug delivery. Since early 2000's, an intracellular drug delivery technique named nanotube spearing using nanomaterial supernatants has been developed. In 2007, Peidong Yang et al. of UC Berkeley, U.S.A. reported a study result of incubation of mice embryonic stem cells using vertically grown silicon nanowires and DNA transfection upon penetrating cells with the nanowires (Kim W, Ng J K, Kunitake M E, Conklin B R, Yang P, J. (2007) Am. Chem. Soc. 128:8990-8991), and suggested a possibility of application of vertically grown nanowires to live cells for the first time, although the transfection efficiency was very low as less than 1%.

SUMMARY OF THE INVENTION

Accordingly, the present inventors successfully established a method to immobilize live cells and specific enzyme substrates to vertically grown nanowires, cultured the cells immobilized to a piece of nanowires with the enzyme substrates immobilized to another piece of nanowires in a sandwich format, and succeeded in measuring the enzyme activity in live cells, to complete the present invention.

Therefore, one embodiment of the present invention provides a method of measuring intracellular activity of a bioactive substance comprising immobilizing cells to nanowires, immobilizing target substance for a bioactive substance to be detected covalently to separate nanowires, culturing the cells together with the target substance in a sandwich format, and detecting reaction of the target substance and/or degree of the reaction inside the cells.

Another embodiment provides a chip for measuring intracellular activity of a bioactive substance including nanowires to which cells are immobilized and nanowires to which target substances for bioactive substance to be detected are immobilized, the cell-immobilized nanowires and the target substance-immobilized nanowires being in contact with each other in a sandwich manner.

Another embodiment provides a kit for measuring intracellular activity of a bioactive substance including said chip for measuring intracellular activity of the bioactive substance and a mean for detecting reaction of the target substance and/or degree of the reaction inside the cells.

DETAILED DESCRIPTION OF THE EMBODIMENTS

The present inventors developed a sandwich assay technology to analyze activity of a bioactive substance such as enzyme in live-cell using vertically grown silicon nanowires. Differently from the existing enzyme activity assay conducted by cell lysis, the assay according to the present invention is designed so as to analyze activity of enzyme in cells with keeping the cells alive, wherein two kinds of vertically grown nanowires, immobilize cells to one nanowires and immobilize target substances for bioactive substance, for example a substrate for an enzyme, to the other nanowires, are provided and cultured in a sandwich manner so that the substrates immobilize to the nanowires may penetrate into the living cells and react with intracellular enzyme.

By observing changes of substrates immobilized on the nanowires due to the reaction with intracellular enzyme through the sandwich assay, a possibility of analyzing specific enzyme activity in live-cell has been suggested. In addition, according to the present invention, it is possible to analyze enzymatic activity in live cell without conducting purification or cell lysis/extraction process.

The present inventors use two supports having vertically grown silicon nanowires on their surfaces; immobilize live cell(s) to the nanowires on one support (support A); establish conditions that do not allow transfer of the cell(s) to nanowires on the other support (support B), when conducting sandwich culture, culture the cell(s) in sandwich manner by overlapping the nanowires to which the cell(s) immobilized to the nanowires on support B, and confirm whether the nanowires on support B are inserted into the cell(s); immobilize a substrate for an enzyme to be detected to nanowires on support B through covalent bonds, overlap the substrate-immobilized nanowires with the cell-immobilized nanowires, culture them in a sandwich manner, and confirm that the substrate covalently immobilized to the nanowires on support B are not discharged into the cell(s) immobilized to the nanowires on support A; and, after conducting sandwich culture, analyze reaction of the enzyme in the live cell(s) immobilized to the nanowires on support A with the substrate immobilized to the nanowires on support B and degree of the reaction.

One embodiment of the present invention provides a method of measuring intracellular activity of a bioactive substance. The method may include the steps of:

culturing a cell together with a support (support A) having nanowires on its surface, and immobilizing the cell to the nanowires, to manufacture a cell-fixed nanowire support;

immobilizing a target substance for a bioactive substance of interest (i.e., to be detected) to nanowires on surface of another support (support B), to manufacture a target substance-fixed nanowire support;

positioning the target substance-fixed nanowire support down and the cell-fixed nanowire support up, overlapping the supports so that the cell-fixed side of the cell-fixed nanowire support and the target substance-fixed side of the targeting substance-fixed nanowire support are in contact with each other, and culturing them; and detecting reaction of the targeting substances on the targeting substance-fixed nanowires or degree of the reaction.

Another embodiment provides a chip for measuring intracellular activity of a bioactive substance, which includes a support (support A) with nanowire(s) to which a cell(s) is(are) immobilized; and another support (support B) with nanowire(s) to which a target substance(s) for the bioactive substance is(are) immobilized. In the chip for measuring intracellular activity of a bioactive substance, the support with the target substance-fixed nanowire(s) is positioned down, the support with the cell-fixed nanowire(s) is positioned up, and the two supported are contacted with each other so that the cell-fixed side and the targeting substance-fixed side are in contact with each other.

Another embodiment provides a kit for measuring intracellular activity of a bioactive substance in a live cell, which includes said chip for measuring intracellular activity of a bioactive substance, and a mean for detecting reaction of the target substance immobilized to the chip and/or degree of the reaction.

Hereinafter, the present invention is explained in detail.

Nanowire

Nanowire commonly refers to a wire structure having a diameter of nanometer (nm) scale. Generally, it includes those having a diameter of less than 10 nm to those having a diameter of several hundred nm, and the length thereof is not specifically limited. As the material, a metal (Ni, Pt, At, etc.), a semiconductor material (Si, InP, GaN, ZnO, etc.), an insulating material ($SiO_2$, $TiO_2$, etc.), and the like may be variously used.

As used herein, the 'nanowire' may be made of any materials that can be oxidized during the synthesis process to form an oxide film on the surface, thereby forming a surface with chemical conditions for which desired substance can be attached to the surface. For examples, the nanowire may be made of at least one selected from the group consisting of Si, ZnO, GaAs, InP, InAs, Ni, Pt, Au, $SiO_2$, $TiO_2$, C, etc. The diameter of the nanowire may be about 1 nm to about 100 nm, and the length, although not specifically limited, may be for example about 500 nm to about 6 nm. Because the nanowire used in the present invention is very thin with a diameter of 100 nm or less, it is advantageous for immobilization of live cells. To conduct effective cell immobilization and sandwich assay, it is preferable to use vertically or almost vertically grown nanowires, for example, grown at an angle of about 45° to about 90° to the support.

And, 'nanowire support' as used herein refers to a commonly used support on which nanowires made of the above described material are formed. The support may be preferably solid for the formation of nanowires, and the material of the support may be at least one selected from the group consisting of Si, ZnO, GaAs, InP, InAs, Ni, Pt, Au, $SiO_2$, $TiO_2$, C, etc., but not limited thereto. Preferably, the 'nanowire support' refers to the above described support on which the nanowires are grown at an angle of about 45° to about 90° thereto.

The nanowire may be surface-modified so as to be favorable for immobilization of cell or target substance. For example, the surface may be silanized, preferably silanized so as to have positively charged ammonium group or amine group. If the surface is silanized, it may become hydrophilic and thus favorable for cell immobilization, and if it has positively charged ammonium group or amine group, it may be favorable for immobilization of desired material. For examples, the nanowire surface may be modified using at least one selected from the group consisting of aminopropyl trimethoxysilane (APTMS), aminopropyl triethoxysilane (APTES), aminopropyl dimethylethoxysilane (APDMES), propyldimethylmethoxysilane (PDMMS), 6-aminohexyl aminomethyltriethoxysilane (AHAMTES), and the like.

Cell, Bioactive Substance, and Target Substance

The cell that can be applied in the present invention may include a live cell as well as a dead cell, and particularly, the present invention can be applied to measure activity of a bioactive substance in live cell.

The cell is not specifically limited, and may be selected from all prokaryotic cells and eukaryotic cells.

The bioactive substance of which activity is to be measured in the present invention refers to any substance acting in live cell, and may be at least one selected from the group consisting of enzymes, antibodies, peptides, proteins, nucleic acids, chemical drugs, and the like. In a concrete embodiment, an enzyme is representatively exemplified as the bioactive substance. For the bioactive substance, counteractive substances and various disturbing environments may exist in cells, and in vitro test may be difficult to measure the exact activity of the bioactive substance because competition and/or disturbance action in living body, such as action of counteraction enzyme, may not be considered. According to the live cell activity assay technique of the present invention, accurate measurement of activity in living body can be achieved.

The target substance refers to a subject substance on which the bioactive substance to be detected acts in a cell, and in terms of functions, it may be a substrate to enzyme, antigen to antibody, drug target to drug, etc., and in terms of components, it may be selected from the group consisting of peptides, proteins, nucleic acids, chemical substances, and the like.

Stable Cell Immobilization to Nanowires

To efficiently measure activity of a bioactive substance in a cell, the cell should be stably fixed to nanowires, and during sandwich culture with target substance-fixed nanowires, they should not transfer to the target substance-fixed nanowires which are positioned down, so as not to affect the final analysis. Thus, in the present invention, a cell is immobilized to nanowires in a living state, and despite the immobilized cells are positioned on the target substance-fixed nanowires, they are stably immobilized without transfer to the target substance-fixed nanowires which are positioned down.

For such stable fixation, the nanowire surface may be silanized, preferably silanized so as to have positively charged ammonium group. In addition, the cell-fixed nanowires may be treated with a mixture (trypsin/EDTA) of trypsin and ethylenediaminetetraacetic acid (EDTA) to remove unstably bound cells, thereby increasing efficiency of stable cell fixation to nanowires (see Example 2 and FIG. 2). The volume ratio of the trypsin and EDTA may be 1:1 to 5:1, preferably 2:1 to 3:1 (trypsin volume:EDTA volume).

As described above, since the nanowires of the present invention have a very small diameter of 100 nm or less, cells may be successfully fixed thereto without cell disruption. In addition, when the nanowires are silanized thereby being hydrophilic, there is an advantage that cells are uniformly fixed. On the other hand, when the nanowires are simply washed and used, due to the hydrophobic surface, cells may not be evenly distributed. The uniform distribution of the cells may allow that the cells can be fixed to the whole surface of the nanowires, and that the fixed cells do not transfer to the other nanowires during sandwich assay, if the cells are cultured for a sufficient time (at least 4 hours, preferably 4 to 24 hours) to be adhered to the nanowire surface and treated with trypsin when conducting cell fixation.

Stable Fixation of Target Substance to Nanowires

In the present invention, the target substance-fixed nanowires, during sandwich culture with the cell-fixed nanowires, may safely enter into the fixed cells's interior so that the target substances fixed on the nanowires may be stably introduced into the cells.

For this, the surface of nanowires on which the target substances are to be fixed may be silanized, preferably silanized so as to have positively charged ammonium group.

The targeting substances may be fixed to the nanowires by any electrochemical bonds, for example, electrostatic bond, covalent bond, for example, amide bond, etc.

In particular, the target substances fixed to the nanowires should be safely penetrated into cells and react with bioactive substances existing in cells, and, even after separated from the cells, the target substances should be stably fixed to the nanowires so as to accurately detect the reaction and degree of the reaction. In this regard, when the target substances are fixed by covalent bonds, most stable fixation may be obtained (Example 4 and FIG. 4). Thus, in a preferable embodiment, the target substances may be fixed to the nanowires by covalent bonds.

An appropriate linker to form covalent bond between the nanowire and the target substance may be used. For example, SMPH(Succinimidyl-6-[β-maleimidopropionamido]hexanoate) may be used as a linker, but not limited thereto. Linkers having amine-reactive N-hydroxysuccinimide (NHS ester) capable of reacting with primary amine of silanized nanowire to form amide bond as a reaction group, and having maleimide functional group capable of forming thiol ester bond with SH group of amino acid at the other end, such as SPDP (N-Succinimidyl 3-(2-pyridyldithio)-propionate), LC-SPDP (Succinimidyl 6-(3-[2-pyridyldithio]-propionamido) hexanoate), Sulfo-SMCC (Sulfosuccinimidyl 4-[N-maleimidomethyl]cyclohexane-1-carboxylate), EMCS ([N-e-Maleimidocaproyloxy]succinimide ester), and the like, may be used.

Sandwich Type and Culture

Sandwich type, sandwich assay, or sandwich culture herein refers to a type, assay or culture conducted while the cell-fixed nanowires and the target substance-fixed nanowires overlap each other so that the cell-fixed side and the target substance-fixed side may be in contact with each other (see FIG. 1).

The incubation conducted when fixing cells to nanowires, and the sandwich culture of the cell-fixed nanowires and the target substance-fixed nanowires may be conducted under common medium and culture conditions depending on the kind of cells, and the conditions may be easily determined according to the kind of cells by one of ordinary knowledge in the art.

Detection of Reaction of Target Substance and/or the Degree

After sandwich culture, reaction of the target substances and/or degree of the reaction may be detected by commonly known methods according to the type of reaction between bioactive substance to be identified and target substance, and the type of a product generated after reaction of target substance.

For example, if the bioactive substance to be identified is restriction enzyme, molecular weight of target substance may be measured after reaction, or if the opposite part of the nanowire bound part is cleaved, the opposite end may be labeled by common means (for example, fluorophores or dyes), and fluorescences or chromophore signals existing in cells after reaction may be determined to detect reaction of the target substances and/or degree of the reaction. And, if the bioactive substance to be identified is an enzyme adding or removing a specific functional group such as kinase or phosphatase, the existence of the functional group on the target substances after reaction may be determined to detect reaction of the target substance and/or degree of the reaction.

The fluorophores or dyes may include any kinds of fluorophores or dyes, and for examples, at least one selected from the group consisting of rhodamine (for example, TAMRA(5-carboxytetramethylrhodamine), dihydrotetramethylrhodamine-4-yl, tetramethylrhodamine-5-yl, tetramethylrhodamine-6-yl, etc.), fluorescein (for example, fluorescein diacetate, fluorescein isothiocyanate (FITC), fluorescein carboxylic acid (FCA), fluorescein thiourea (FTH), fluorescein-5-yl, fluorescein-6-yl, 2',7'-dichlorofluorescein-5-yl, 2',7'-dichlorofluorescein-6-yl, etc.), coumarin (for example, 7-acetoxycoumarin-3-yl, etc.), indacene (4,4-difluoro-5,7-dimethyl-4-bora-3a,4a-diaza-s-indacene-3-ethyl and 4,4-difluoro-5,7-diphenyl-4-bora-3a,4a-diaza-s-indacene-3-ethyl, etc.), but not limited thereto.

The detection of reaction of target substance and/or the degree may be easily determined by one of ordinary knowledge in the art according to the kind of bioactive substance to be identified and the type of reaction with target substance.

Basic concept of the present invention is schematically shown in FIG. 1. FIG. 1 is a schematic drawing of sandwich assay identifying activity of specific bioactive substance (for example, enzyme) in cells using vertically grown silicon nanowires and target substances (for example, substrate peptide) according to one embodiment. Cells are immobilized to silicon nanowires of one side (UP), and substrate peptides for enzyme to be identified are immobilized to silicon nanowires of the other side (DOWN) using a linker (for example, SMPH (Succinimidyl-6-[β-maleimidopropionamido]hexanoate) linker), and then, the substrate peptide-fixed silicon nanowires are positioned down and the cell-fixed silicon nanowires are put thereon so as to contact with each other, and incubated for a time sufficient for reaction of the substrate peptide, and then, change of the substrate peptides of the lower silicon nanowires is analyzed to determine enzyme activity inside the cells.

As explained, a method for measuring enzyme activity in live cells without destroying the cells using nanowire-based sandwich assay is designed, thereby establishing novel cell-based assay platform to suggest a possibility to use for various kinds of enzymes and various kinds of bioactive substances.

BRIEF DESCRIPTION OF DRAWINGS

FIG. 9 shows the results of measuring intracellular protein kinase A activity by mass analysis of substrate peptide for protein kinase A through sandwich assay.

EXAMPLE

The present invention is further explained in more detail with reference to the following examples. These examples, however, should not be interpreted as limiting the scope of the present invention in any manner.

Example 1

Preparation of Vertically Grown Silicon Nanowires

According to the reported literatures (*J. Am. Chem. Soc.* 2008, 130, 6252-6258; *NanoLett.* 2004, 4, 1987-1990; *J. Am. Chem. Soc.* 2001, 123, 9769-9779; *J. Am. Chem. Soc.* 2008, 130, 6252-6258), colloidal Au nanoparticles (Ted Pella, USA; 50 nm in diameter) were dispersed and immobilized onto a Si(111) substrate to prepare a substrate.

On the prepared substrate, vertically grown silicon nanowires were synthesized with minor modifications of the method reported in the reference (*NanoLett.* 2005, 5, 457-460) according to the chemical vapor deposition (CVD) method. At this time, $SiCl_4$ was used as a precursor for growing nanowires, and $H_2$(10%)-containing argon was used as carrier gas.

The Au nanoparticle-distributed Si(111) substrate was introduced in a quartz tube with 1 inch diameter, which was loaded in a 12 inch horizontal tube furnace (Lindberg/Blue M). The quartz tube was deflated, and repeatedly flushed with $H_2$(10%)-containing argon gas mixture, and then, pressure was raised to 760 torr, and a pump line was immediately switched to a vent line so that gas phase HCl generated by decomposition of $SiCl_4$ may be trapped through a bubbler filled with aqueous $K_2CO_3$ solution. The temperature of the furnace was elevated at a speed of 16.6° C./min, and when 840° is reached, the flow rate of the $H_2$(10%)-containing argon gas was reduced from 1000 SCCM (standard cubic centimeters per minute) to 250 SCCM.

Figure 7:
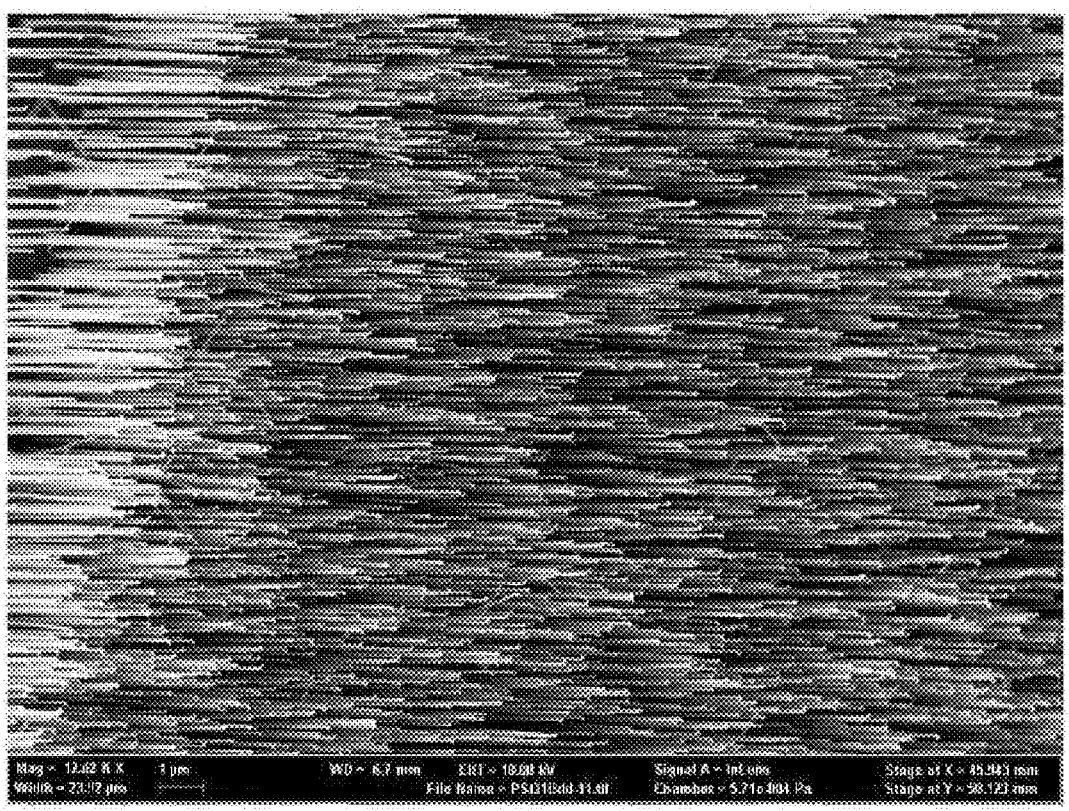
FIG. 7 is an SEM photo of vertically grown silicon nanowires, taken in the tilted stage for verification of vertical growth.

In order to transfer saturated $SiCl_4$ to a reaction zone, a second stream of $H_2$(10%)-containing argon gas of 50 SCCM was passed through the bubbler filled with $SiCl_4$. After reaction for 10 minutes, a valve of the bubbler was closed and 50 SCCM of argon gas was purged to rapidly cool the quartz tube. Vertical growth of silicon nanowires on the Si substrate was examined by SEM (scanning electron micrography), and the result is shown in FIG. 7. The obtained silicon nanowire support was cut into a size of ~2 mm×5 mm and used in the following experiments.

Example 2

Experiment of Cell Fixation to Silicon Nanowires

To test cell fixation efficiency of the vertically grown silicon nanowires prepared in Example 1, HeLa cells were fixed as follows, and the degree of fixation was tested.

In order to efficiently conduct the experiment of analyzing enzyme activity using silicon nanowires, cells should be stably fixed to cell-fixed silicon nanowires, and during incubation with substrate peptide-fixed nanowires, cells should not transfer to the opposite nanowires so as not to affect the final analysis step. Thus, a method is optimized to stably fix cells to silicon nanowires and prevent transfer of the cells to peptide-fixed silicon nanowires during the reaction. The Example was conducted on the basis of the existing study result that vertically grown silicon nanowires penetrate cells by gravity upon incubation with cells and the cells penetrated by the vertically grown nanowires may be stably kept alive for one week or longer (Kim W, Ng J K, Kunitake M E, Conklin B R, Yang P, J. Am. Chem. Soc. 128 (2007):8990-8991).

First, vertically grown silicon nanowires were incubated with HeLa cells for one day to immobilize the cells to the silicon nanowires, and cells pricked by the silicon nanowires and cells surface-attached superficially without being penetrated by the nanowires were removed by treatment with trypsin, and then, fluorescein diacetate was utilized to visualize cells to identify the degree of transfer to the opposite nanowires by fluorescence microscope.

Specifically, the silicon nanowires prepared in Example 1 were washed with 100% (v/v) isopropyl alcohol before use and dried at room temperature, and then, introduced in 2 ml toluene solution containing 100 µl APTMS (Aminopropyl trimethoxysilane), reacted for 2 hours, washed three times respectively with toluene, 100% ethanol, and distilled water, and finally washed with PBS (Phosphate Buffered Saline) to complete silanization so that the surface of the silicon nanowire has positively charged ammonium group. Then, HeLa cells (ATCC, USA) were added on top of nanowires, followed by incubation at 37° C., 5% $CO_2$, for one day in DMEM medium (GIBCO, USA) containing penicillin (100 units/ml), streptomycin (0.1 mg/ml) and 10% FBS, in order to immobilize the cells to the nanowires having silanized surface.

The cell-immobilized nanowires were treated with PBS solution that contains or does not contain trypsin/EDTA (a mixture of 0.025 vol % of trypsin (GIBCO) and 0.01 vol % of EDTA (GIBCO)) for 10 minutes, washed with PBS, and then, separate silicon nanowires having silanized surface were overlapped thereon, and incubated at 37° C., 5% $CO_2$, for one day in DMEM medium (GIBCO, USA) containing penicillin (100 units/ml), streptomycin (0.1 mg/ml) and 10% FBS.

At this time, the silicon nanowires to which cells are not fixed were positioned down, the cell-fixed silicon nanowires were positioned up, and they were cultured in a sandwich format so as to contact with each other. In order to see if cells transfer from the cell-fixed silicon nanowires to non cell-fixed silicon nanowires, both pieces of nanowires were introduced in DMEM medium containing fluorescein diacetate (Berry & Associates) at concentration of 10 µM, and then, dyed at 37° C., 5% CO2 for 20 minutes. This is a commonly used method for labeling live cells with flourophore wherein fluorescein diacetate enters into cells and, if esterase in the cell acts, is hydrolyzed to a carboxylic acid form and trapped in the cell. After washing with PBS buffer, the cell immobilization was identified using fluorescence microscope (480 nm excitation/520 nm emission).

Figure 1:
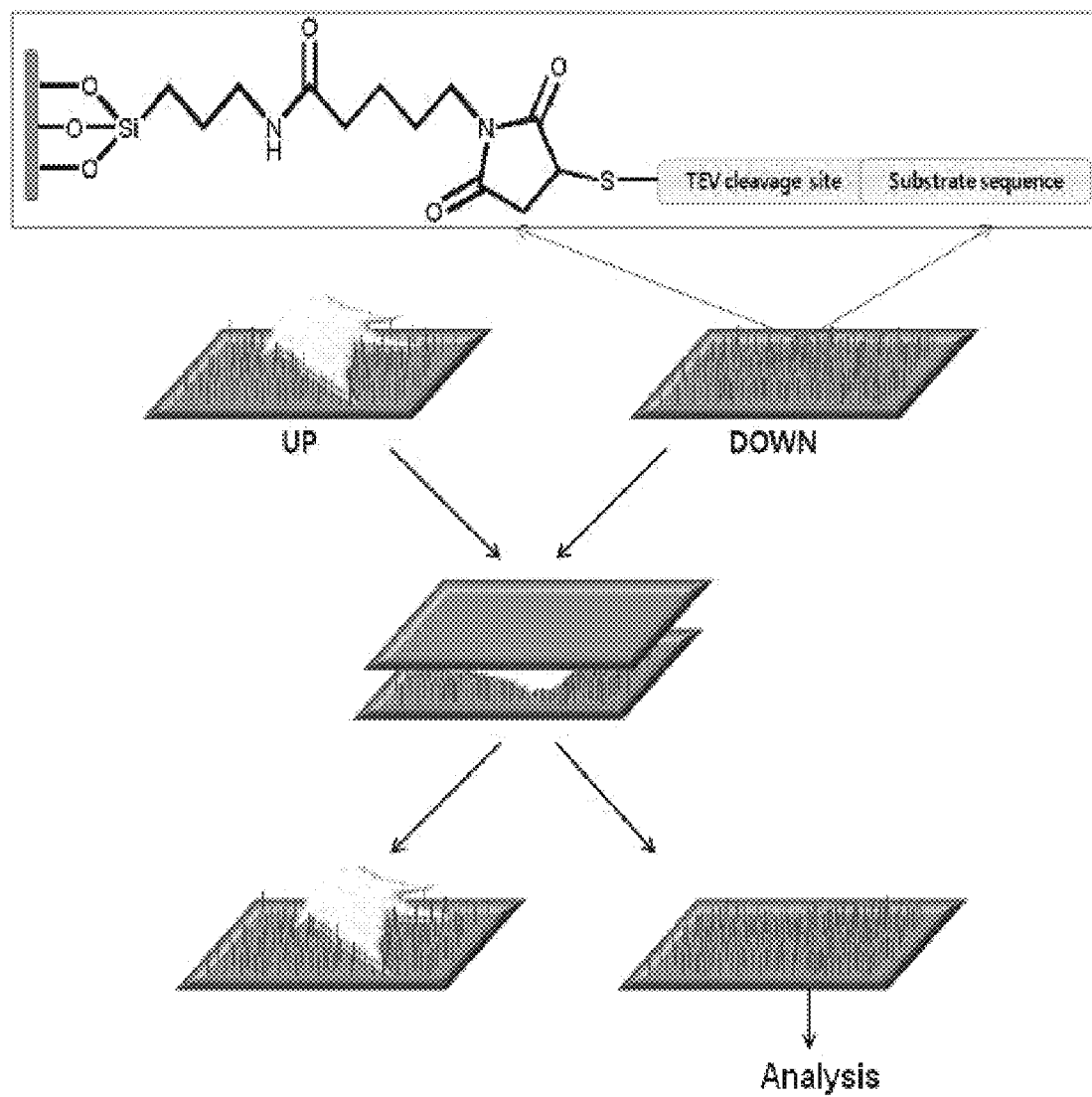
FIG. 1 is a schematic drawing of sandwich assay identifying activity of specific enzyme in cells using vertically grown silicon nanowires and substrate peptides.
Figure 2:
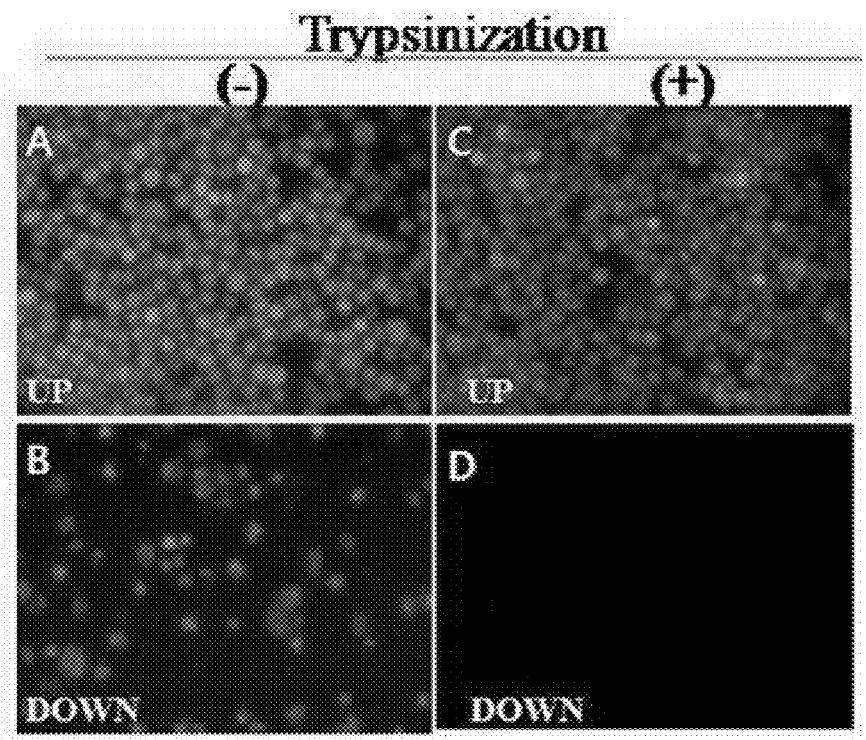
FIG. 2 is a fluorescence microscope image of cells showing difference according to trypsin treatment when HeLa cells are immobilized to silicon nanowires and cultured with another silicon nanowires in a sandwich format.

The results are shown in FIG. 2. A and B of FIG. 2, which show the results when the silicon nanowires were not treated with trypsin/EDTA solution, are fluorescence microscope images of cells on the upper and lower silicon nanowires, after the cell-immobilized nanowires were sandwich cultured with separate silicon nanowires. A is a fluorescence microscope image of the cells on the cell-immobilized silicon nanowires, and B is a fluorescence microscope image of the cells which transferred to the opposite nanowires contacting with the cell-immobilized silicon nanowires in a sandwich manner during cell incubation. The result shows that some of the cells immobilized to the upper nanowires transferred to the lower nanowires. FIGS. 2C and 2D, which show the results when the silicon nanowires were treated with trypsin/EDTA solution to remove unstably bound cells, are fluorescence microscope images of the cells respectively on the upper and lower silicon nanowires, after cells were immobilized to the nanowires, treated with trypsin/EDTA, and sandwich cultured with separate silicon nanowires. C is a fluorescence microscope of the cells on the cell-immobilized silicon nanowires, and D is a fluorescence microscope of the cells which transferred to the opposite nanowires contacting with the cell-immobilized silicon nanowires in a sandwich manner.

As shown in FIG. 2, in case the silicon nanowires were not treated with trypsin/EDTA, it was observed that some of the cells immobilized to the upper silicon nanowires transferred to the lower silicon nanowires, while in case the silicon nanowires were treated with trypsin/EDTA, transfer of cells immobilized to the upper silicon nanowires to the lower silicon nanowires was not observed. The result shows that when cells are incubated with silicon nanowires, and then, treated with trypsin/EDTA, and sandwich cultured with separate nanowires, transfer of the cells from the originally immobilized nanowires to the opposite nanowires may be prevented.

Example 3

Molecular Delivery into Cells Using Silicon Nanowires

To test if the opposite nanowires enter into the cells immobilized to nanowires when incubated in a sandwich manner, stable introduction of specific molecules into cells using silicon nanowires was confirmed.

First, silicon nanowires were surface-silanized with APTMS by the same method as in Example 2, and incubated with HeLa cells in a DMEM medium containing penicillin (100 units/ml), streptomycin (0.1 mg/ml) and 10% FBS (fetal bovine serum) for one day at 37° C., 5% $CO_2$, and then, treated with a PBS solution containing trypsin/EDTA for 10 minutes to prepare nanowires to which the cells are stably fixed.

Separate silicon nanowires were surface-silanized with APTMS, and 5 µl of T15 oligonucleotides comprising 15 T and rhodamine tethered at one end were put thereon at concentration of 100 pmol/µl and dried at room temperature to electrostatically attach the oligonucleotides to the nanowires, and then, sandwich cultured with the cell-fixed silicon nanowires in DMEM medium containing penicillin (100 units/ml), streptomycin (0.1 mg/ml) and 10% FBS for one day at 37° C., 5% $CO_2$. After incubation, the degree of delivery of the oligonucleotides electrostatically attached to silicon nanowires to the cells immobilized to nanowires was identified with a fluorescence microscope.

Figure 3:
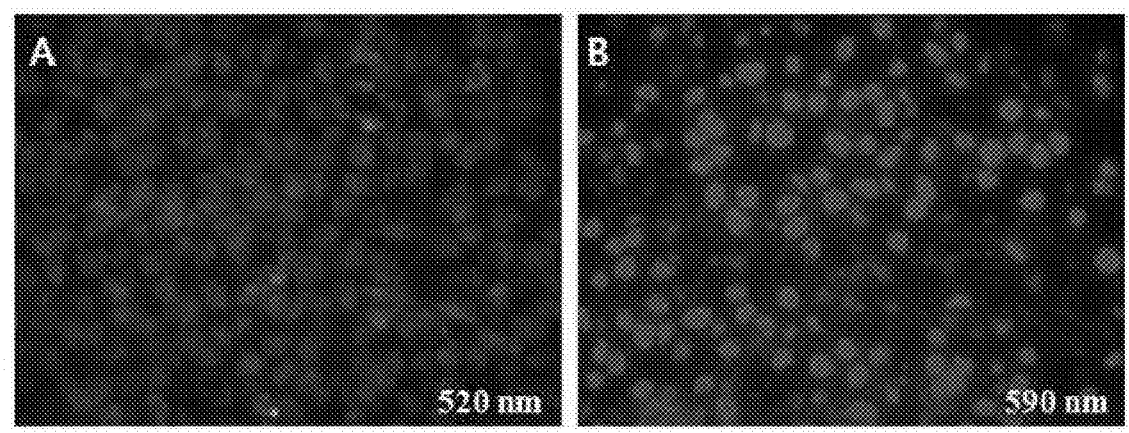
FIG. 3 is a fluorescence microscope image observing transfer of rhodamine-labeled oligonucleotides into cells, after HeLa cell-fixed nanowires are cultured with nanowires to which rhodamine-labeled oligonucleotides are electrostatically attached.

The results are shown in FIG. 3. FIG. 3A is a fluorescence microscope image identifying cells immobilized to silicon nanowires (480 nm excitation/520 nm emission, over-exposure), and B is a fluorescence microscope image identifying rhodamine-labeled oligonucleotides entering into the cells (555 nm excitation/590 nm emission). FIG. 3 shows that if two nanowires, after sandwich culture, are separated and the cell-fixed nanowire is observed with a fluorescence microscope, rhodamine-labeled oligonucleotides exist in the cell. This result means that during sandwich culture, oligonucleotide-fixed silicon nanowires penetrate into the cells and oligonucleotides electrostatically bound to the nanowires are discharged in the cells. Thus, it is confirmed by sandwich assay that materials fixed to nanowires of one side effectively permeate into the cells fixed to the opposite nanowires.

Example 4

Confirmation of Stability of Peptide Immobilized Covalently to Silicon Nanowire

To conduct an experiment identifying intracellular enzyme activity using silicon nanowires, enzyme substrate peptides fixed covalently to silicon nanowires should not be discharged into the cells during sandwich culture with cell-fixed nanowires and should be stably bound to the silicon nanowires until analysis step. Thus, electrostatic bonding of substrate peptides to nanowires, and immobilizing of the substrate peptides by covalent bonds using an SMPH (Succinimidyl-6-[β-maleimidopropionamido]hexanoate) linker were compared.

Cell-fixed nanowires were prepared as in Example 2. To electrostatically attach the substrate peptides to nanowires, 5 μl of PBS solution containing 500 μM of FITC (fluorescein isothiocyanate)-labeled peptides (GGGGENLYQGGGG (SEQ NO. 4)-Ahx_C—NH$_2$ (Ahx=6-aminohexanoic acid)) was added to silicon nanowires which were surface-silanized using APTMS.

Meanwhile, in order to immobilize the substrate peptides to nanowires by covalent bonds using SMPH linker, silicon nanowires which were surface-silanized with APTMS were introduced in 500 μl of PBS buffer containing 500 μM of SMPH linker (Pierce, USA), and reacted at room temperature for 2 hours so that the amine of the nanowire surface and NHS(N-hydroxysuccinimide ester) of the SMPH linker form stable amide bonds. And then, it was rinsed with PBS and a PBS solution containing 500 μM of FITC-labeled peptides was introduced and reacted at room temperature for 12 hours so that a thioester bond forms between the —SH group of cysteine existing at the C-terminus of the peptide and maleimide of SMPH.

The nanowires to which peptides are fixed by each method were washed with PBS and positioned down, and the cell-fixed nanowires were positioned up, and they are contacted with each other in a sandwich manner, and then, incubated in DMEM medium containing penicillin (100 units/ml), streptomycin (0.1 mg/ml) and 10% FBS at 37° C., 5% CO$_2$ for 12 hours. After incubation, the cell-fixed nanowires and the peptide-fixed nanowires were separated, and the cell-fixed nanowires were examined with a fluorescence microscope to confirm entrance of the peptides in the cells.

Figure 4:
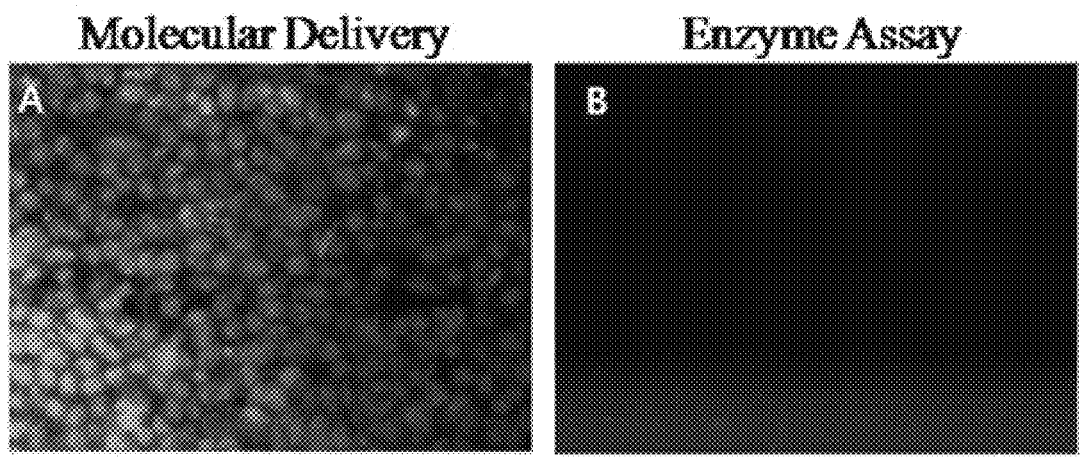
FIG. 4 is a fluorescence microscope image observing delivery of substrate peptides to cells after substrate peptide-fixed nanowires are sandwich cultured with HeLa cell-fixed silicon nanowires, in case the substrate peptides are fixed to the nanowires by (A) electrostatic bonds, and (B) covalent bonds.

The results are shown in FIG. 4. FIG. 4A shows the result when the substrate peptides are electrostatically attached to the nanowire, and B shows the result when the substrate peptides are covalently bonded to the nanowire using SMPH linker. As shown in FIG. 4A, it is confirmed that when the peptides are electrostatically attached to the nanowire, the peptides are discharged in the cells during incubation with the cell-fixed nanowires, and in contrast, as shown in FIG. 4B, it is confirmed that when the peptides are fixed to the nanowires by covalent bonds using SMPH linker, the peptides are not discharged in the cells during incubation with the cell-fixed nanowires. In conclusion, it can be seen that if peptides are fixed to nanowires by covalent bonds, peptide stability may be secured during assay to enable conducting of perfect and effective sandwich assay.

Example 5

Identification of Activity of Intracellular Protein Tyrosine Phosphatase (PHP) by Sandwich Assay Using Silicon Nanowires Protein phosphorylation plays important roles for controlling enzyme activity, cell signaling, protein-protein interaction, protein stability, etc. The protein phosphorylation is balanced and controlled by kinase and phosphatase existing in cells. Among phosphatases, protein tyrosine phosphatase (PTP) recognizes phosphorylated tyrosine and dephosphorylates it thereby controlling protein phosphorylation to control various biological phenomena occurring in cells. In addition, various kinds of PTPs exist, and it is active in all the cells irrespective of the kind of cell, thus selected as a first assay subject.

5.1. Preparation of Substrate Peptide for PTP

First, a substrate peptide for PTP was prepared. A cysteine residue was added at the C-terminus of the peptide so as to form thioether bond with maleimide group of SMPH(Succinimidyl-6-[β-maleimidopropionamido]hexanoate).

In addition, in order to analyze whether the reaction occurs or not by MOLDI-TOF (Matrix Assisted Laser Desorption/Ionization Time-of-Flight), peptide parts should be separated from the nanowires to which the peptides are fixed by covalent bonds. For this, it is required to insert a sequence which is cleaved by a specific protease, and thus, Glu-Asn-Leu-Tyr-Phe-Gln-Gly sequence that is recognized by TEV (Tobacco Etch Virus) protease (highly site-specific cysteine protease) that does not exist in mammal cells is added to the C-terminus of the peptide so that a region between Gln and Gly is recognized and cleaved by TEV protease. And, phosphorylated tyrosine was bonded to the N-terminus of the peptide.

As explained, the substrate peptide for PTP was prepared (purchased and synthesized by AnyGen (Korea, Gwang-ju): pYGGGGENLYFQGGGG (SEQ NO. 1)-Ahx_C—NH$_2$ (Ahx=6-aminohexanoic acid)).

5.2. Fixation of Cells and Substrate Peptides to Silicon Nanowires

For sandwich assay experiment, HeLa cells were fixed to the vertically grown silicon nanowires prepared in Example 1.

Specifically, the silicon nanowires prepared in Example 1 were washed with 100% (v/v) isopropyl alcohol before use and dried at room temperature, and then, introduced in 2 ml of toluene solution containing 100 μl of APTMS (Aminopropyl trimethoxysilane), reacted at room temperature for 2 hours, and washed 3 times respectively with toluene, 100% ethanol and distilled water, and finally washed with PBS (Phosphate Buffered Saline) to complete silanization so that the surface of the silicon nanowire has positively charged ammonium group. HeLa cells (ATCC) were incubated with the nanowires having silanized surface in DMEM medium (GIBCO) containing penicillin (100 units/ml), streptomycin (0.1 mg/ml, GIBCO) and 10% FBS (GIBCO) at 37° C., 5% CO$_2$ to immobilize the cells to the nanowires having silanized surface.

To separate silicon nanowires, SMPH(Succinimidyl-6-[β-maleimidopropionamido]hexanoate) linkers were covalently bonded as in Example 4, and then, the PBS solution containing 100 μM of PTP substrate peptides prepared in Example 5.1 was added and reacted at room temperature for 12 hours, and washed with PBS.

5.3. Measurement of PTP Activity

The cell-fixed nanowires were positioned down, the PTP substrate peptide-fixed nanowires were positioned up, and they were contacted with each other, and then, incubated in DMEM medium containing penicillin (100 units/ml), streptomycin (0.1 mg/ml), and 10% FBS at 37° C., 5% CO$_2$ for 1 hour. After incubation, the cell-fixed silicon nanowires and the peptide-fixed nanowires were separated from each other, and the peptide-fixed nanowires were washed with PBS and introduced in a buffer containing 50 mM Tris-HCl, pH 7.5, 0.5 mM EDTA, and 1 mM DTT (Dithiothreitol), and TEV protease (10 units/150 μl, Invitrogen) were added and treated at room temperature for 2 hours, and then, desalting was conducted with Zip-TIP (MILLIPORE), and changes of peptides were analyzed by MALDI-TOF (Applied Biosystems).

Figure 5:
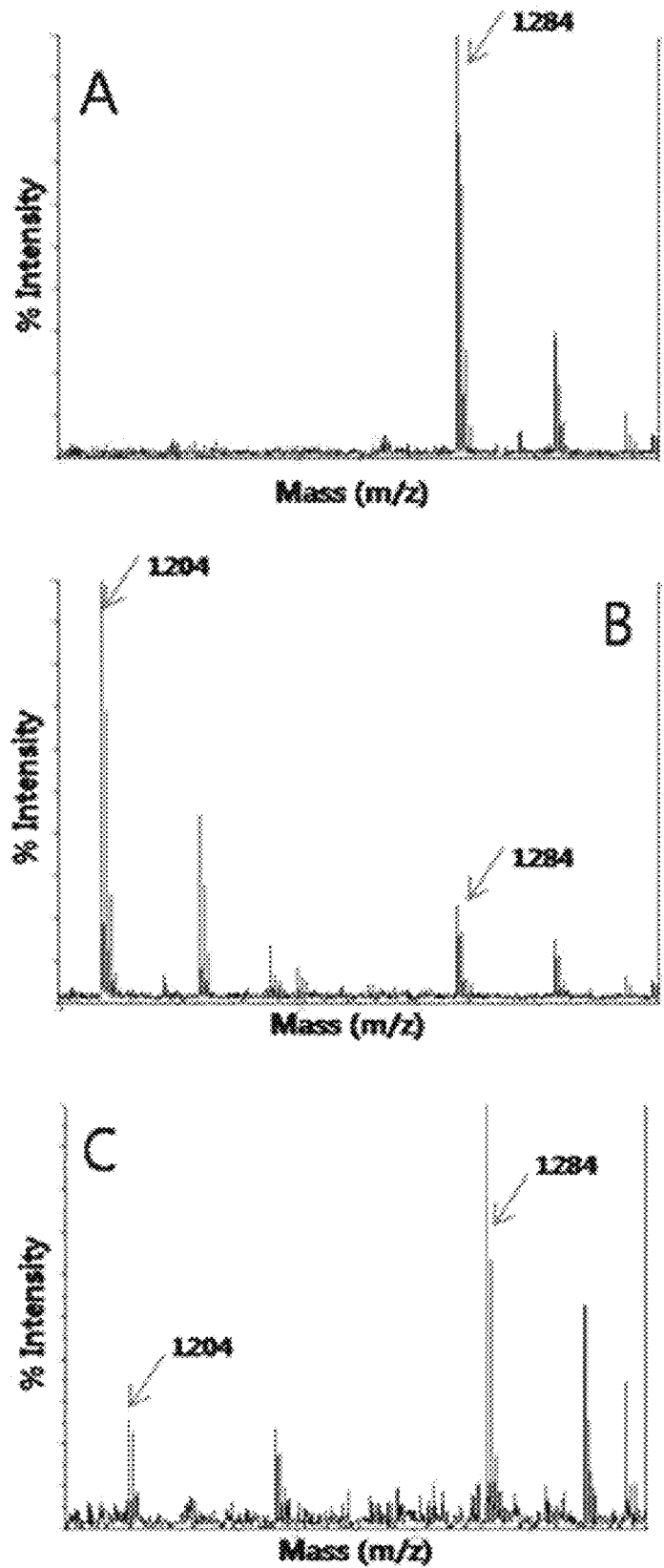
FIG. 5 shows the results of measuring intracellular PTP (Protein tyrosine phosphatase) activity by mass analysis of substrate peptide for PTP through sandwich assay.

The results are shown in FIGS. 5A and 5B. FIG. 5A shows the results of analyzing peptides isolated by treating TEV protease after incubating in DMEM medium containing penicillin (100 units/ml), streptomycin (0.1 mg/ml) and 10% FBS at 37° C., 5% $CO_2$ for 1 hour, and it confirms stable bonding of the peptides to the silicon nanowires. As shown in FIG. 5A, a mass peak is shown only at 1284 dalton, which is an expected peptide peak. From this result, it is confirmed that peptides fixed to the nanowires by covalent bonds are stably fixed in the medium, and there is no change of peptides in the medium.

To the contrary, FIG. 5B shows MALDI-TOF result analyzing peptides isolated after peptide-fixed nanowires were incubated with cell-fixed nanowires for 1 hour and treated with TEV protease, and it is confirmed that phosphotyrosine existing at N-terminal of the peptide is dephosphorylated by PTP to produce a mass peak at 1204 dalton. This result shows that substrate peptides enter into the cells and are reacted by phosphatase in the cells during sandwich assay.

In order to reconfirm that change of the peptides fixed to the nanowires is caused by the reaction of phosphatase in the cells, chemical inhibitors were treated and the same experiment was conducted. As PTP inhibitors, sodium orthovanadate (phosphate analogue reversibly acting on enzyme active site to inhibit protein tyrosine phosphatase, alkaline phosphatase and ATPases, Sigma) and α-bromo-4-hydroxyacetophenone (binding to the catalytic domain of phosphatase including SH2 domain to inhibit the activity of phosphatase, Calbiochem) were used.

Cell-fixed silicon nanowires were incubated in DMEM medium containing penicillin (100 units/ml), streptomycin (0.1 mg/ml), 10% FBS and 100 μM sodium orthovanadate and 40 μM α-bromo-4-hydroxyacetophenone at 37° C., 5% $CO_2$ for 40 minutes, and then, incubated with the PTP substrate peptide-fixed nanowires in DMEM medium containing penicillin (100 units/ml), streptomycin (0.1 mg/ml), 10% FBS and 100 μM sodium orthovanadate and 40 μM α-bromo-4-hydroxyacetophenone at 37° C., 5% $CO_2$ for 1 hour.

After incubation, the peptide-fixed nanowires were treated with TEV protease and the isolated peptides were analyzed by MALDI-TOF, and the result is shown in FIG. 5C. As shown in FIG. 5C, 1204 dalton peak is remarkably reduced, reconfirming that dephosphorylation in FIG. 5B is caused by the action of phosphatase in the cells.

Example 6

Identification of Intracellular Caspase Activity by Sandwich Assay Using Silicon Nanowires Caspase, which is one of cystein proteases, plays important roles in apoptosis (programmed cell death), necrosis, inflammation, development, and etc., and some of caspases are required to control the immune system for cytokine growth. Loss of the caspase activity leads to inhibition of apoptosis, which may be the main cause of tumor development, autoimmune disease, and etc. Thus, caspases attract attention as a therapeutic target capable of controlling the above diseases and studies thereon are actively progressed.

Among them, apoptotic caspases are classified into two types of initiator (apical) caspases and effector (executioner) caspases. The initiator caspases (CASP2, CASP8, CASP9, CASP10) cleave pro-forms of the effector caspases to allow the caspases to become active, and the effector caspases (CASP3, CASP6, CASP7) recognize and cleave specific sites of various different kinds of substrate proteins to induce apoptosis. And, the caspase activity is controlled by caspase inhibitors.

In this example, change in intracellular caspase activity upon apoptosis induction was confirmed by nanowire-based sandwich assay using substrate peptides for caspases. After confirming the cleavage motif recognized by the effector caspases and the initiator caspases, substrate peptides for caspases were constructed so as to include DEVDG sequence recognized and cleaved by caspases (CASP1, CASP2, CASP3, CASP6, CASP7, CASP9) (AADEVDGGGGENLY-FQGGGG(SEQ NO. 2)-Ahx-C—$NH_2$). And then, in order to visualize caspase activity in cells, fluorescence dye TAMRA (5-carboxytetramethylrhodamine) was bonded to the N-terminus of the cleavage motif sequence to construct a substrate peptide (final peptide: TAMRA-AADEVDGGGGENLY-FQGGGG(SEQ NO. 2)-Ahx-C—$NH_2$, purchased and synthesized by AnyGen).

Using the peptides, if cells are treated with apoptosis inducing agent, capases are activated, and DEVDG sequence is recognized by the activated caspases and cleaved at site between aspartate and glycine, and thus, the formed peptide fragments remain in the cells. Since the fragments released into cells have TAMRA dye and can be identified by fluorescence microscope, activation of caspases may be confirmed based thereon.

As described in Example 5, peptides were fixed to nanowires using SMPH linker, and the peptide-fixed nanowires were positioned down, cell-fixed nanowire were positioned up, and they were contacted in a sandwich manner and incubated in DMEM containing penicillin (100 units/ml), streptomycin (0.1 mg/ml), 10% FBS and 200 nM Staurosporine (apoptosis inducing agent, Sigma) at 37° C., 5% $CO_2$ for 4 hours.

Figure 6:
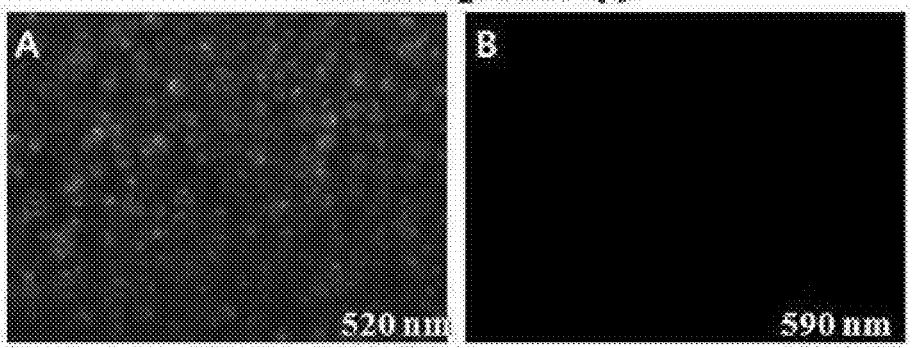
FIG. 6 is a fluorescence microscope image showing the test results of identifying intracellular caspase activity by sandwich assay in Example 6 using a fluorophore (TAMRA).
Figure 6:
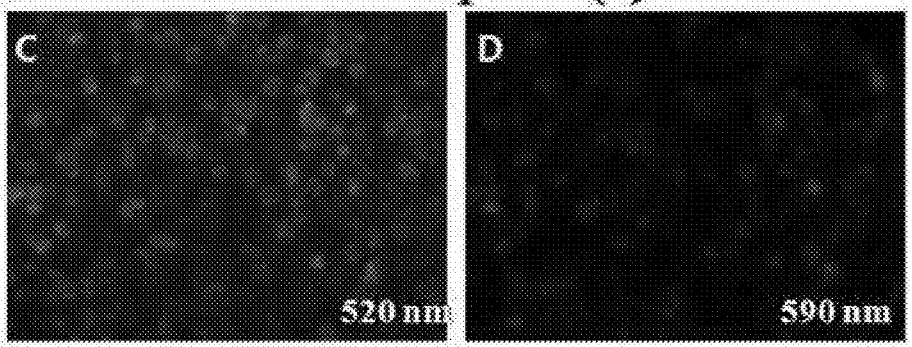

After incubation, the cell-fixed nanowires were identified by fluorescence microscope and the results are shown in FIG. 6. FIGS. 6A and B are fluorescence microscope images identifying the cells fixed to nanowires when the medium does not contain apoptosis inducing agent, and A confirms cell distribution at 480 nm excitation/520 nm emission and B confirms whether or not TAMRA dye-containing peptide fragments are released into the cells by the action of caspases at 555 nm excitation/590 nm emission. Thus, it can be seen that when the medium does not contain apoptosis inducing agent, substrate peptides on the nanowires are not released into the cells. FIGS. 6C and D are fluorescence microscope images when the medium is treated with 200 nM of apoptosis inducing agent, and C confirms cell distribution at 480 nm excitation/520 nm emission, and D confirms the existence of TAMRA dye-containing peptide fragments released into the cells by the action of caspases at 555 nm excitation/590 nm emission, showing the fluorescent cells. The result indicates that intracellular caspases are activated to cleave substrate peptides on the nanowires, and thus TAMRA dye-containing fragments are released into the cells.

Figure 8:
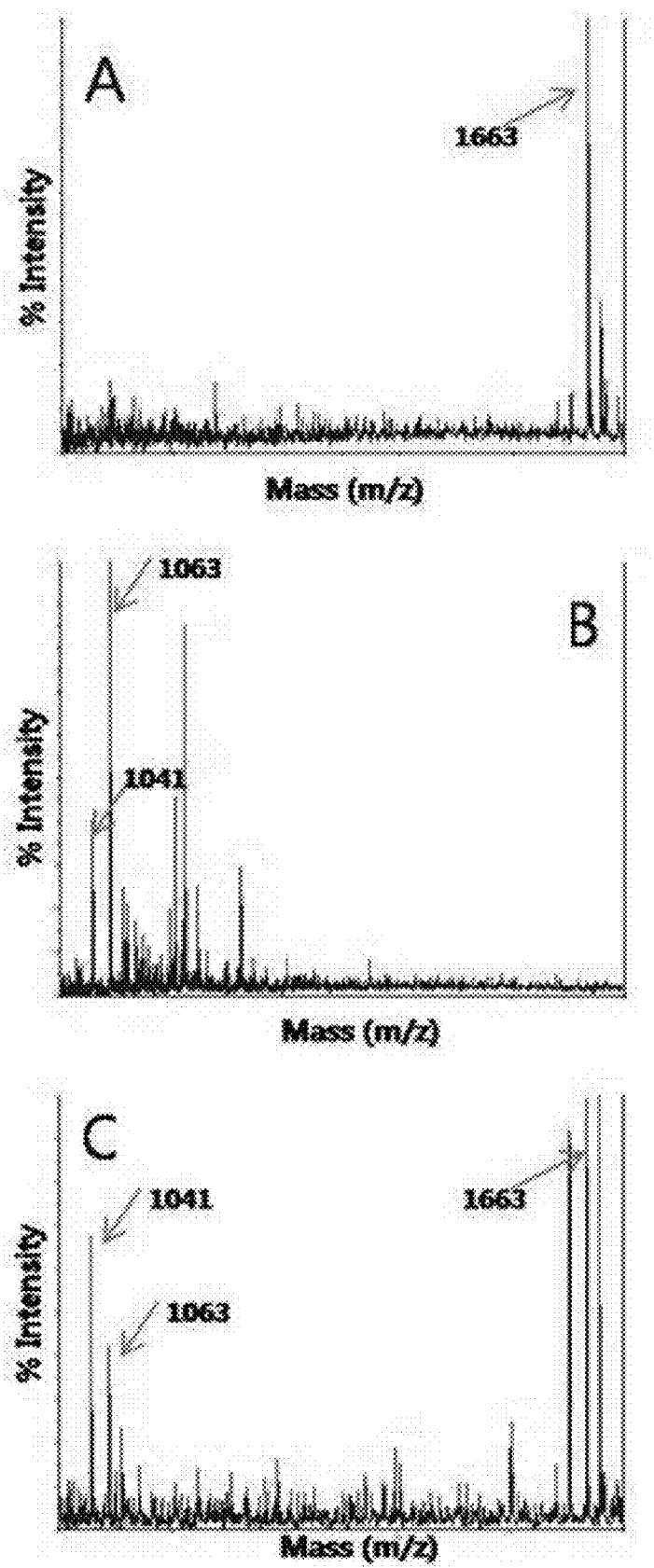
FIG. 8 shows the results of measuring intracellular caspase activity by mass analysis of substrate peptide for caspase through sandwich assay.

And, for mass analysis of caspase activity upon treatment of apoptosis inducing agent, peptide that does not contain TAMRA dye (AADEVDGGGGENLYFQGGGG(SEQ NO. 2)-Ahx-C—$NH_2$) was prepared (purchased and synthesized by AnyGen), and the activity was confirmed by nanowire-based sandwich assay and the results are shown in FIG. 8.

A of FIG. 8 shows the MALDI-TOF result of analyzing peptides isolated by treating TEV protease (Invitrogen) after incubating in DMEM medium containing penicillin (100 units/ml), streptomycin (0.1 mg/ml) and 10% FBS at 37° C., 5% $CO_2$ for 1 hour, and it confirms stable bonding of the peptides to the silicon nanowires. As shown in FIG. 8A, a mass peak is shown only at 1663 dalton, which is an expected peptide peak.

To the contrary, B of FIG. 8 shows MALDI-TOF result analyzing peptides isolated after peptide-fixed nanowires are incubated under PBS containing 10 µg/ml of isolated and purified caspase 3 (BioVision, USA) for 1 hour and treated with TEV protease, and it is confirmed that most of substrate peptides are cleaved by caspase3 to produce a mass peak of 1041 dalton C of FIG. 8 shows MALDI-TOF result analyzing peptides isolated by treating peptide-fixed nanowires with TEV protease after immobilizing peptides to nanowires using SMPH linker, positioning cell-fixed nanowires up and peptide-fixed nanowires down, contacting them in a sandwich manner, and incubating in DMEM medium containing penicillin (100 units/ml), streptomycin (0.1 mg/ml), 10% FBS and 500 nM Staurosporine (apoptosis inducing agent, Sigma) at 37° C., 5% $CO_2$ for 18 hours. It is confirmed that caspase substrate peptides fixed to nanowires are cleaved by caspase activated by staurosporine to produce a mass peak of 1041 dalton.

Example 7

Identification of Intracellular Protein Kinase A Activity by Sandwich Assay Using Silicon Nanowires Protein kinase chemically adds a phosphate group to substrate molecules to change enzyme activity, cellular location or association with other proteins, and thus change the function of substrates. Activity of protein kinase A, which is one of the protein kinases, (one of serine/threonine-specific protein kinases, catalyzing phosphorylation of OH group of serine or threonine of substrate molecules, and the activity of protein kinase A being controlled dependently upon the concentration of intracellular cyclic AMP) in cells was measured by sandwich assay.

In this example, the degree of activity of intracellular protein kinase A upon treatment of Forskilin which is known to increase intracellular cyclic AMP concentration was confirmed by nanowire-based sandwich assay using protein kinase A substrate peptide. LRRASL sequence-containing peptide which is recognized and phosphorylated by protein kinase A was prepared (final peptide: LRRASLGGENLY-FQGGGG (SEQ NO. 3)-Ahx-C—NH$_2$, purchased and synthesized by AnyGen), and confirmed by nanowire-based sandwich assay and the results are shown in FIG. 9.

A of FIG. 9 shows the MALDI-TOF result of analyzing peptides isolated by treating TEV protease after incubating in DMEM medium containing penicillin (100 units/ml), streptomycin (0.1 mg/ml) and 10% FBS at 37° C., 5% $CO_2$ for 1 hour, and it confirms stable bonding of the peptides to the silicon nanowires. As shown in FIG. 9A, a mass peak is shown only at 1624 dalton, which is an expected peptide peak.

To the contrary, B of FIG. 9 shows MALDI-TOF result analyzing peptides isolated after peptide-fixed nanowires are incubated with 2,500 units of PKA (NEW ENGLAND BioLabs) in pH 7.5 PBS containing 50 mM Tris-HCl, 10 mM $MgCl_2$ and 200 µM ATP at 30° C. for 1 hour and treated with TEV protease, and it is confirmed that serine residues in most of substrate peptides are phosphorylated by protein kinase to produce a mass peak of 1703 dalton C of FIG. 9 shows MALDI-TOF result of peptides isolated by treating peptide-fixed nanowires with TEV protease after immobilizing peptides to nanowires using SMPH linker, positioning the peptide-fixed nanowires down and cell-fixed nanowires up, contacting them in a sandwich manner, and incubating them in DMEM medium containing penicillin (100 units/ml), streptomycin (0.1 mg/ml), 10% FBS and 30 µM Forskolin (Sigma) and phosphatase inhibitor cocktail (Sigma) at 37° C., 5% $CO_2$ for 30 minutes. It is confirmed that protein kinase does not cause any change in substrate peptides for protein kinase A fixed to nanowires.

D of FIG. 9 shows MALDI-TOF result analyzing change in protein kinase A substrate peptides by protein kinase A after fixing peptides to nanowires using SMPH Linker, positioning the peptide-fixed nanowires down and cell-fixed nanowires up, contacting them in a sandwich manner, and incubating them in DMEM medium containing penicillin (100 units/ml), streptomycin (0.1 mg/ml), 10% FBS and 30 µM Forskolin (Sigma) and phosphatase inhibitor cocktail (Sigma) at 37° C., 5% $CO_2$ for 20 minutes. Production of a mass peak of 1703 dalton is confirmed, which is considered to be formed by the activity of protein kinase A.

In conclusion, the above results show that if cells are treated with forskolin, cAMP increases and protein kinase A is activated to phosphorylate the substrate, but with the lapse of time, the phosphorylated substrate is dephosphorylated again (phosphorylated peak appears at 20 minutes and disappears at 30 minutes). Thus, the present invention enables measurement of dynamic change of enzyme activity in live cells.

What is claimed is:

1. A method of measuring intracellular activity of a bioactive substance, the method comprising:
preparing a first nanowire support by binding a first nanowire on a first support such that the first nanowire forms at an angle of about 45° to 90° to a support surface of the first support;
preparing a second nanowire support by binding a second nanowire on a second support such that the second nanowire forms at an angle of about 45° to 90° to a support surface of the second support;
culturing a cell with the first nanowire support, thereby immobilizing the cell to the first nanowire, to manufacture a cell-fixed nanowire support;
immobilizing a target substance for the bioactive substance to the second nanowire support, to manufacture a target substance-immobilized nanowire support;
positioning the cell-fixed nanowire support on the target substance-immobilized nanowire support such that a cell-immobilized side of the cell-fixed nanowire support and a target substance-immobilized side of the target substance-immobilized nanowire support are in contact with each other, and culturing the cell-fixed nanowire support and the target substance-immobilized nanowire support that are in contact; and
detecting a reaction of the targeting substance on the target substance-immobilized nanowire support, or measuring a degree of the reaction.

2. The method according to claim 1, wherein each of the first and second nanowires has a diameter of 1 nm to 100 nm.

3. The method according to claim 1, wherein each of the first and second nanowires is formed of at least one selected from the group consisting of Si, ZnO, GaAs, InP, InAs, Ni, Pt, Au, SiO$_2$, TiO$_2$, and C.

4. The method according to claim 1, wherein each of the first and second nanowires has a silanized surface.

5. The method according to claim 4, wherein the silanization is conducted using at least one selected from the group consisting of APTMS (Aminopropyl trimethoxysilane), APTES (Aminopropyl triethoxysilane), APDMES (Aminopropyl dimethylethoxysilane), PDMMS (propyldimethylmethoxysilane), and AHAMTES (6-aminohexyl aminomethyltriethoxysilane).

6. The method according to claim 1, wherein the manufacturing of the cell-fixed nanowire support comprises treating the cell-immobilized nanowire with a mixture of trypsin and ethylenediaminetetraacetic acid (EDTA).

7. The method according to claim 6, wherein the mixture of trypsin and ethylenediaminetetraacetic acid (EDTA) comprises trypsin and ethylenediaminetetraacetic acid at a volume ratio of 1:1 to 5:1 (the volume of trypsin:the volume of ethylenediaminetetraacetic acid).

8. The method according to claim 1, wherein the manufacturing of the target substance-immobilized nanowire support is conducted by immobilizing the target substance to the second nanowire through covalent bonds.

9. The method according to claim 8, wherein the target substance is covalently bonded to the second nanowire through a linker having amine-reactive hydrosuccinimide at one end and a maleimide group at the other end.

10. The method according to claim 9, wherein the linker is selected from the group consisting of SMPH (Succinimidyl-6-[β-maleimidopropionamido]hexanoate), SPDP (N-Succinimidyl 3-(2-pyridyldithio)-propionate), LC-SPDP (Succinimidyl 6-(3-[2-pyridyldithio]-propionamido)hexanoate), Sulfo-SMCC (Sulfosuccinimidyl 4[N-maleimidomethyl]cyclohexane-1-carboxylate), EMCS ([N-e-Maleimidocaproyloxy]succinimide ester), and a combination thereof.

11. The method according to claim 1, wherein the bioactive substance is selected from the group consisting of enzyme, antibody, peptide, protein, nucleic acid, chemical drug, and a combination thereof.

12. The method according to claim 1, wherein the target substance is selected from the group consisting of peptide, protein, nucleic acid, chemical substance, and a combination thereof.

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: substrate peptide for protein tyrosine
      phosphatase
<220> FEATURE:
<221> NAME/KEY: MOD_RES
<222> LOCATION: (1)
<223> OTHER INFORMATION: PHOSPHORYLATION,

<400> SEQUENCE: 1

Tyr Gly Gly Gly Gly Glu Asn Leu Tyr Phe Gln Gly Gly Gly Gly
 1               5                  10                  15
```

```
<210> SEQ ID NO 2
<211> LENGTH: 20
<212> TYPE: PRT
<213> ORGANISM: Artificial Sequence
<220> FEATURE:
<223> OTHER INFORMATION: substrate peptide for caspase

<400> SEQUENCE: 2

Ala Ala Asp Glu Val Asp Gly Gly Gly Glu Asn Leu Tyr Phe Gln
 1               5                  10                  15

Gly Gly Gly Gly
            20

<210> SEQ ID NO 3
<211> LENGTH: 18
<212> TYPE: PRT
<213> ORGANISM: Artificial Sequence
<220> FEATURE:
<223> OTHER INFORMATION: substrate peptide for protein kinase A

<400> SEQUENCE: 3

Leu Arg Arg Ala Ser Leu Gly Gly Glu Asn Leu Tyr Phe Gln Gly Gly
 1               5                  10                  15

Gly Gly

<210> SEQ ID NO 4
<211> LENGTH: 13
<212> TYPE: PRT
<213> ORGANISM: Artificial Sequence
<220> FEATURE:
<223> OTHER INFORMATION: amino acid sequence of FITC(fluorescein
      isothiocyanate)-labeled peptide

<400> SEQUENCE: 4

Gly Gly Gly Gly Glu Asn Leu Tyr Gln Gly Gly Gly Gly
 1               5                  10
```